United States Patent

(12) United States Patent
Lin

(10) Patent No.: US 10,682,433 B2
(45) Date of Patent: Jun. 16, 2020

(54) APPARATUS FOR AUTOMATICALLY DISINFECTING PIPING FOR MEDICAL USES

(71) Applicant: Yu Tsung Lin, New Taipei (TW)

(72) Inventor: Yu Tsung Lin, New Taipei (TW)

(*) Notice: Subject to any disclaimer, the term of this patent is extended or adjusted under 35 U.S.C. 154(b) by 168 days.

(21) Appl. No.: 16/100,278

(22) Filed: Aug. 10, 2018

(65) Prior Publication Data

US 2020/0046866 A1    Feb. 13, 2020

(51) Int. Cl.
*A61L 2/18*     (2006.01)
*A61L 2/24*     (2006.01)
*A61B 90/70*    (2016.01)
*A61B 1/12*     (2006.01)

(52) U.S. Cl.
CPC ............... *A61L 2/18* (2013.01); *A61B 90/70* (2016.02); *A61L 2/24* (2013.01); *A61B 1/123* (2013.01); *A61B 1/125* (2013.01); *A61B 2090/701* (2016.02)

(58) Field of Classification Search
CPC . A61L 2/18; A61L 2/183; A61L 2/186; A61L 2/24; A61B 90/70; A61B 1/123; A61B 1/125; A61B 2090/701
See application file for complete search history.

(56) References Cited

U.S. PATENT DOCUMENTS

| | | | | |
|---|---|---|---|---|
| 6,142,170 A | * | 11/2000 | Belfer ................. | A61C 1/0076 137/240 |
| 6,250,920 B1 | * | 6/2001 | Overmyer ............ | A61C 1/0076 433/80 |
| 8,506,885 B2 | * | 8/2013 | Kotsos ................ | A61M 1/1686 210/636 |

* cited by examiner

Primary Examiner — Timothy C Cleveland

(57) ABSTRACT

An apparatus for automatically disinfecting piping for medical uses includes a main controller including a control center module, an administration controller, and an electric valve controller; a disinfection solution machine connected to a main pipe including first branch pipes each provided with an administration motor control valve and connected to medical devices, second branch pipes each connected to the first branch pipe, and drains each connected to the first branch pipe, first electric valves each is provided between the medical device and the first branch pipe, second electric valves each is provided in the second branch pipe, third electric valves each is provided in the drain; and a reverse osmosis water filter being in fluid communication with a purified water reservoir having an outlet connected to the first branch pipes, and a feedback end connected to the second branch pipes.

5 Claims, 2 Drawing Sheets

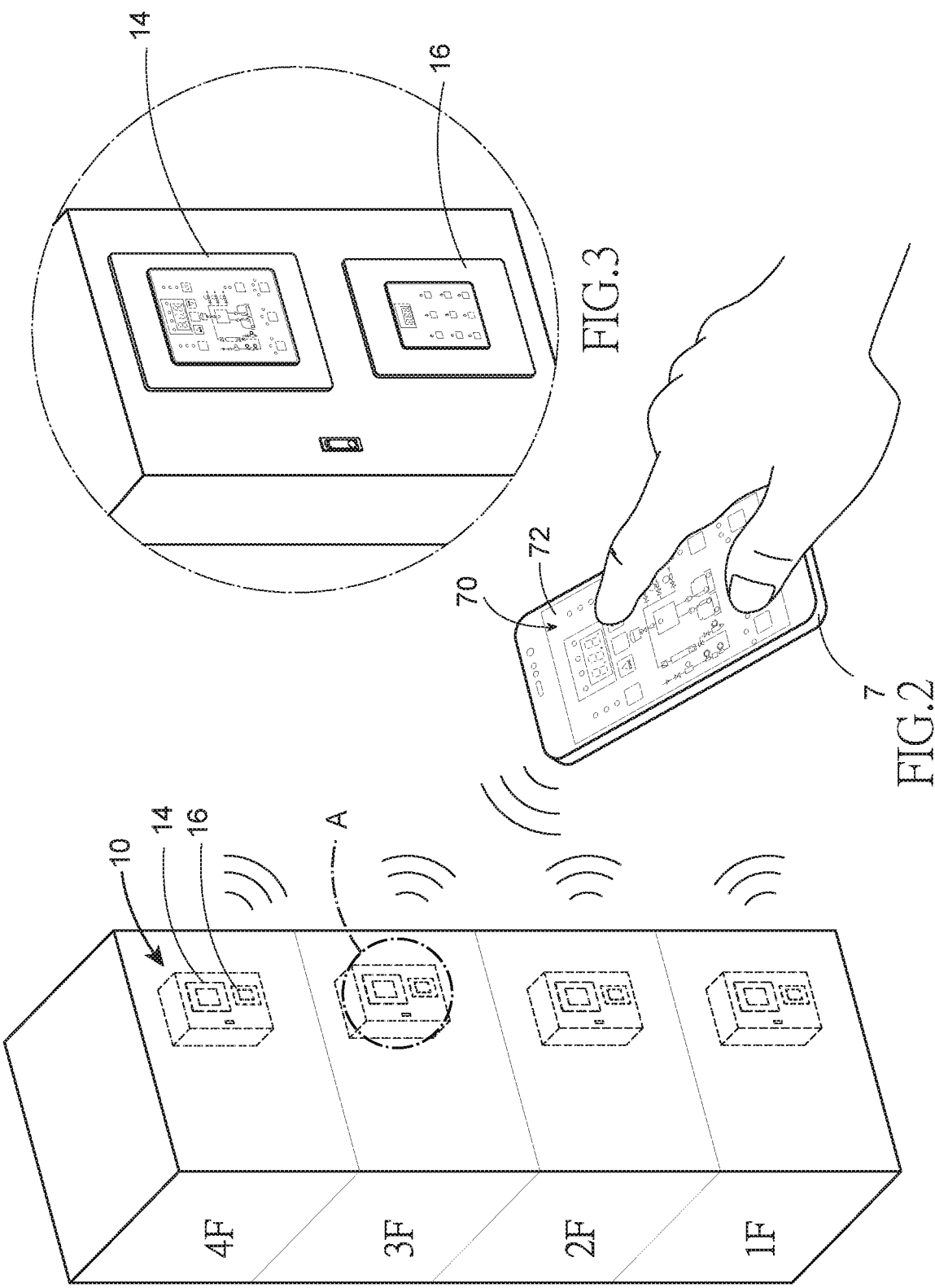

APPARATUS FOR AUTOMATICALLY DISINFECTING PIPING FOR MEDICAL USES

BACKGROUND OF THE INVENTION

1. Field of the Invention

The invention relates to piping disinfection and more particularly to an apparatus for automatically disinfecting piping for medical uses in which a main controller is used to mix disinfection solution with water purified by a reverse osmosis water filter so that the piping and any medical devices connected to the piping can be cleaned and disinfected.

2. Description of Related Art

Piping of a hospital is required to clean and disinfect regularly for sanitary purposes. Typically, a medical employee may add hydrogen peroxide and peracetic acid to a reservoir stored with water purified by means of reverse osmosis. As such, a disinfection solution is made in the reservoir. However, the manual cleaning and disinfection has the following drawbacks.

1. Limited time for disinfection: The manual cleaning and disinfection is usually done on weekends for preventing from interfering with the clinical hours of a hospital. Also, the cleaning workers have to do the cleaning of many hospitals. Thus, a thorough cleaning and disinfection of drains of piping and medical devices is made impossible in the short weekends.

2. Time consuming and labor intensive: The cleaning and disinfection is typically taken biweekly or monthly. Also, too much time is spent on a single medical device. Thus, batch cleaning and disinfection of the medical devices is inefficient.

3. Low cleaning and disinfection quality: The manual cleaning and disinfection is low in quality. It is impossible of ensuring a thorough cleaning and disinfection. After the cleaning and disinfection, a detailed check of the piping and the medical devices is required. Otherwise, the cleaning and disinfection quality is doubtful.

Thus, the need for improvement still exists.

SUMMARY OF THE INVENTION

It is therefore one object of the invention to provide an apparatus for automatically disinfecting piping for medical uses comprising a main controller including a control center module, an administration controller electrically connected to the control center module, and an electric valve controller electrically connected to the control center module; a disinfection solution machine electrically connected to the administration controller and connected to a main pipe including at least one first branch pipe each provided with an administration motor control valve and connected to at least one medical device, at least one second branch pipe each connected to the first branch pipe, and at least one drain each connected to the first branch pipe wherein at least one first electric valve each is provided between the medical device and the first branch pipe, at least one second electric valve each is provided in the second branch pipe, at least one third electric valve each is provided in the drain, the administration controller is electrically connected to the administration motor control valve, and the electric valve controller is electrically connected to the at least one first electric valve, the at least one second electric valve and the at least one third electric valve respectively; and a reverse osmosis water filter electrically connected to the control center module and being in fluid communication with an inlet of a purified water reservoir wherein an outlet of the purified water reservoir is connected to the at least one first branch pipe, a feedback end of the purified water reservoir is connected to the at least one second branch pipe, and at least one pump each is provided in the first branch pipe for transferring fluids.

Preferably, in sterilization, the main controller instructs the disinfection solution machine to generate disinfection solution. Purified water generated by the reverse osmosis water filter is mixed with the disinfection solution in the main pipe to form a mixture. The electric valve controller opens the first and third electric valves and closes the second electric valves to transfer a portion of the mixture to the medical devices via the first branch pipes and the first electric valves. As a result, the medical devices are disinfected. Further, the remaining portion of the mixture is transferred to the drains for discharge after passing through the first branch pipes and the third electric valves. As a result, the first branch pipes are disinfected.

The invention has the following advantages and benefits in comparison with the conventional art:

1. No time limit for disinfection: The cleaning and disinfection can be done by operating the main controller at any time (e.g., in the nights) as long as the medical devices are not in use. Thus, the factors of hospital closing and locations are not taken into consideration.

2. Automation: The cleaning and disinfection can be done by operating the main controller only. Progress of the cleaning and disinfection can be monitored in real time. Many medical devices can be cleaned and disinfected in the same time. Thus, efficiency is increased greatly.

3. Improved quality: Quality of the cleaning and disinfection is improved due to the automation. No more unacceptable quality of the cleaning and disinfection.

The above and other objects, features and advantages of the invention will become apparent from the following detailed description taken with the accompanying drawings.

BRIEF DESCRIPTION OF THE DRAWINGS

FIG. 2 schematically depicts using a smart device to operate the apparatus installed in each floor of a hospital; and FIG. 3 is a detailed view of the area in a circle A of FIG. 2.

DETAILED DESCRIPTION OF THE INVENTION

Figure 1:
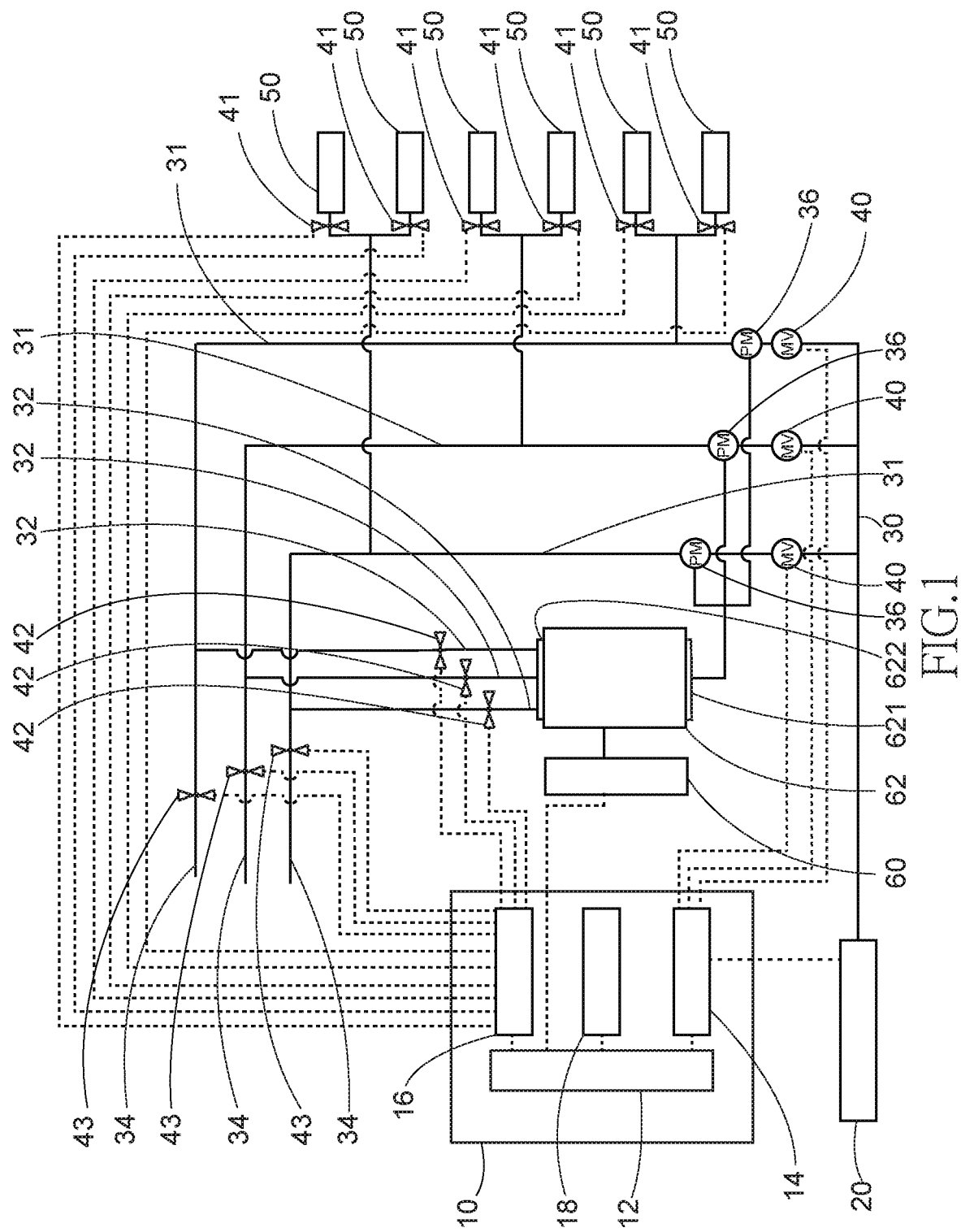
FIG. 1 schematically depicts an apparatus for automatically disinfecting piping for medical uses according to the invention.

Referring to FIGS. 1 to 3, an apparatus for automatically disinfecting piping for medical uses in accordance with the invention comprises a main controller 10, a disinfection solution machine 20 and a reverse osmosis water filter 60 as discussed in detail below.

The main controller 10 includes a control center module 12, an administration controller 14 electrically connected to the control center module 12, and an electric valve controller 16 electrically connected to the control center module 12.

The disinfection solution machine 20 is electrically connected to the administration controller 14 and connected to a main pipe 30 including a plurality of first branch pipes 31 each provided with an administration motor control valve 40 and connected to a plurality of (two are shown) medical devices 50. The main pipe 30 further comprises a plurality of second branch pipes 32 each connected to the first branch pipe 31, and a plurality of drains 34 each also connected to the first branch pipe 31.

A plurality of first electric valves 41 each are provided between the medical device 50 and the first branch pipe 31. A plurality of second electric valves 42 each are provided in the second branch pipe 32. A plurality of third electric valves 43 each are provided in the drain 34. The administration controller 14 is electrically connected to the administration motor control valves 40. The electric valve controller 16 is electrically connected to the first electric valves 41, the second electric valves 42 and the third electric valves 43 respectively. The reverse osmosis water filter 60 is electrically connected to the control center module 12 and is in fluid communication with an inlet of a purified water reservoir 62. An outlet 621 of the purified water reservoir 62 is connected to the first branch pipes 31. A plurality of pumps 36 each are provided in the first branch pipe 31 for transferring fluids. A feedback end 622 of the purified water reservoir 62 is connected to the second branch pipes 32.

Preferably, the first, second and third electric valves 41, 42 and 43 are electromagnetic valves.

Preferably, in sterilization, the electric valve controller 16 opens the first and third electric valves 41 and 43, and closes the second electric valves 42. For using water from the reverse osmosis water filter 60, the electric valve controller 16 opens the first and second electric valves 41 and 42, and closes the third electric valves 43.

Starting sterilization and stopping sterilization (or no sterilization) of the invention are discussed in detailed by referring to FIGS. 1 and 2 below.

Starting Sterilization:

1. The main controller 10 instructs the disinfection solution machine 20 to generate disinfection solution. And in turn, the disinfection solution machine 20 mixes chlorine dioxide or hydrogen peroxide with peracetic acid to generate disinfection solution. The generated disinfection solution flows to the main pipe 30. Further, the reverse osmosis water filter 60 is instructed to generate water by means of reverse osmosis. The generated purified water flows to the purified water reservoir 62 for temporary storage. Further, water in the purified water reservoir 62 discharges through the outlet 621. As a result, purified water flows to the first branch pipes 31. The administration controller 14 activates the administration motor control valves 40 and the pumps 36 to transfer the disinfection solution in the main pipe 30 to the first branch pipes 31 via the administration motor control valves 40 and the pumps 36. As a result, the disinfection solution and the purified water are mixed (called mixture hereinafter).

2. Further, the electric valve controller 16 opens the first and third electric valves 41 and 43, and closes the second electric valves 42 to transfer a portion of the mixture to the medical devices 50 via the first branch pipes 31 and the first electric valves 41. As a result, the medical devices 50 are disinfected. The used mixture discharges from a drain of each medical device 50 without returning to the first branch pipes 31.

3. Furthermore, the remaining portion of the mixture is transferred to the drains 34 for discharge after passing through the first branch pipes 31 and the third electric valves 43. The first branch pipes 31 are disinfected. It is noted that the discharge contains chemicals and disinfected membranes.

Stopping Sterilization (or No Sterilization):

1. The administration controller 14 instructs the disinfection solution machine 20 to stop generating disinfection solution. And in turn, the disinfection solution machine 20 close the administration motor control valves 40. Also, the administration controller 14 instructs the electric valve controller 16 to close the third electric valves 43, and keeps the first and second electric valves 41 and 42 in an open state.

2. The reverse osmosis water filter 60 is instructed to generate water by means of reverse osmosis. The generated purified water flows to the purified water reservoir 62 for temporary storage. Further, water in the purified water reservoir 62 discharges through the outlet 621. As a result, purified water flows to the second branch pipes 32 via the second electric valves 42 and the first branch pipes 31. Thus, the purified water returns to the purified water reservoir 62 via the feedback end 622.

3. A medical employee may activate the electric valve controller 16 to open the first electric valves 41 so that the purified water may pass the first electric valves 41 to flow to the medical devices 50 for consumption.

Referring to FIG. 2 in conjunction with FIG. 1, the control center module 12 is electrically connected to a wireless receiver module 18 which is capable of wirelessly receiving signals transmitted from a synchronous operating software 70 installed in a smart device 7. The synchronous operating software 70 has a simulation control panel 72. A person may press buttons of the simulation control panel 72 to execute the synchronous operating software 70. And in turn, signals are transmitted from the synchronous operating software 70 to the wireless receiver module 18. Further, the control center module 12 receives the signals from the wireless receiver module 18 and in response monitors quality of the purified water and activates (or deactivates) the electric valve controller 16 or the administration controller 14. In brief, the main controller 10 can be controlled in a remote manner.

Preferably, the wireless receiver module 18 is provided with a subscriber identity module (SIM card), a Bluetooth® device, or a Wi-Fi device.

It is envisaged by the invention that the apparatus for automatically disinfecting piping for medical uses has applications in piping that needs to be cleaning regularly such as piping of a hemodialysis room in a hospital, and medical devices disposed on a dental chair.

While the invention has been described in terms of preferred embodiments, those skilled in the art will recognize that the invention can be practiced with modifications within the spirit and scope of the appended claims.

What is claimed is:

1. An apparatus for automatically disinfecting piping for medical uses, comprising:
a main controller including a control center module, an administration controller electrically connected to the control center module, and an electric valve controller electrically connected to the control center module;
a disinfection solution machine electrically connected to the administration controller and connected to a main pipe including at least one first branch pipe each provided with an administration motor control valve and connected to at least one medical device, at least one second branch pipe each connected to the first branch pipe, and at least one drain each connected to the first branch pipe wherein at least one first electric valve each is provided between the medical device and the first branch pipe, at least one second electric valve each is provided in the second branch pipe, at least one third electric valve each is provided in the drain, the administration controller is electrically connected to the administration motor control valve, and the electric valve controller is electrically connected to the at least one first electric valve, the at least one second electric valve and the at least one third electric valve respectively; and a reverse osmosis water filter electrically connected to the control center module and being in fluid communication with an inlet of a purified water reservoir wherein an outlet of the purified water reservoir is connected to the at least one first branch pipe, a feedback end of the purified water reservoir is connected to the at least one second branch pipe, and at least one pump each is provided in the first branch pipe for transferring fluids;

wherein in sterilization, the electric valve controller opens the at least one first electric valve and opens the at least one third electric valve, and closes the at least one second electric valve; and wherein in using purified water from the reverse osmosis water filter, the electric valve controller opens the at least one first electric valve and opens the at least one second electric valve and closes the at least one third electric valve.

2. The apparatus for automatically disinfecting piping for medical uses of claim 1, wherein the control center module is electrically connected to a wireless receiver module which is capable of wirelessly receiving signals transmitted from a synchronous operating software installed in a smart device; and wherein the synchronous operating software has a simulation control panel configured to operate to execute the synchronous operating software so as to remotely control the control center module to monitor quality of the purified water and activates or deactivates the electric valve controller or the administration controller.

3. The apparatus for automatically disinfecting piping for medical uses of claim 1, wherein the wireless receiver module is provided with a subscriber identity module (SIM card), a Bluetooth® device, or a Wi-Fi device.

4. The apparatus for automatically disinfecting piping for medical uses of claim 1, wherein the disinfection solution is made by mixing chlorine dioxide or hydrogen peroxide with peracetic acid.

5. The apparatus for automatically disinfecting piping for medical uses of claim 1, wherein each of the at least one first electric valve is an electromagnetic valve, each of the at least one second electric valve is an electromagnetic valve, and each of the third electric valve is an electromagnetic valve.

* * * * *